United States Patent [19]

Seghizzi et al.

[11] Patent Number: 5,320,841
[45] Date of Patent: Jun. 14, 1994

[54] ORAL PHARMACEUTICAL COMPOSITIONS CONTAINING ANTHOCYANOSIDES

[75] Inventors: Robert Seghizzi; Bruno Gabetta; Paolo Morazzoni, all of Milan, Italy

[73] Assignee: IdB Holding S.p.A., Milan, Italy

[21] Appl. No.: 57,352

[22] Filed: May 3, 1993

[30] Foreign Application Priority Data

May 11, 1992 [IT] Italy .................. MI92 A 001123

[51] Int. Cl.$^5$ .................. A61K 35/78; A61K 9/64; A61K 9/36
[52] U.S. Cl. .................. 424/195.1; 424/451; 424/456; 424/480; 424/501; 514/774; 514/781; 514/783; 514/788; 514/959; 514/962
[58] Field of Search .................. 424/195.1, 451, 456, 424/480, 501; 514/774, 781, 783, 788, 959, 962

[56] References Cited

U.S. PATENT DOCUMENTS 4,413,004 11/1983 Lietti et al. .................. 424/283

Primary Examiner—Thurman K. Page
Assistant Examiner—Jyothsna Venkat
Attorney, Agent, or Firm—Bucknam and Archer

[57] ABSTRACT

Oral pharmaceutical compositions containing high content anthocyanosides, preferably higher than 80% w/w, suspended in fractionated coconut oil have higher bioavailability than water solutions or suspensions in other lipophilic carriers.

7 Claims, No Drawings

ORAL PHARMACEUTICAL COMPOSITIONS CONTAINING ANTHOCYANOSIDES

The present invention relates pharmaceutical compositions for oral use containing extracts with high content in anthocyanosides (HCA) as the active principle.

The fruits of many plants, such as *Vaccinium myrtillus, Ribes nigrum, Vitis vinifera* and *Sambucus nigra*, are starting materials for the preparation of anthocyanosides containing extracts, which are used in therapy in the conditions of impaired microcirculation and in ophthalmology for the treatment of myopias and visual fatigue.

The pharmacological activity of these extracts is mainly due to their content of anthocyanosides. In the *V. myrtillus* fruits, for instance 3-O-galactosides and 3-O-arabinosides of cyanidin, delphinidin, petunidin, peonidin and malvidin aglycones are present in well defined ratios. The anthocyanoside content in the commercial *V. myrtillus* extracts ranges from 2 to 40%.

The present trend is generally to prepare standardized and normalized high content extracts, i.e. containing more than 50% and preferably more than 80% of anthocyanosides (w/w). With this object, a process for the preparation of high content (>80%) anthocyanosides extracts (HCA), in the natural ratios, starting from fruits or from low content extracts, has been recently developed (EP 0412300 A2).

Tests of oral administration in the animal of HCA aqueous solutions have however shown a low absorption of these active principles having flavilium salts structure, which are poorly bioavailable notwithstanding their good water solubility. To improve their oral absorption, the administration of HCA suspended in lipophilic carriers, comprising vegetable oils, such as peanut oil, soybean oil (i.e. long chain fatty acids triglycerides mixtures), semisynthetic vegetable oils, such as fractionated coconut oil (i.e. medium chain fatty acids triglycerides mixtures), unsaturated polyglycolised glycerides (GPGI) and mineral oil, such as liquid paraffin, has been studied.

It has surprisingly been found that fractionated coconut oil is the only carrier, among the cited ones, capable of remarkably improving the oral absorption of HCA when used as a suspending medium.

The present invention relates therefore to pharmaceutical compositions containing high content anthocyanosides (HCA), particularly having a content higher than 50% and preferably higher than 80% (w/w), suspended in fractionated coconut oil, these compositions substantially improving the oral absorption of the active principles.

The suspensions are prepared by suspending micronized HCA in the fractionated coconut oil, at room temperature, by means of a turbine stirrer. HCA are suspended in the lipophilic carrier in percentages ranging from 2% to 10% w/w, preferably from 4 to 8%. Conventional rheological modifiers can also be added to optimize the physical stability of the suspensions, as well as conventional surfactants, such as soybean lecithin, to ensure a good wettability of the HCA powder.

The resulting oily suspensions may then be directly distributed in gelatine capsules or absorbed on suitable excipients, such as colloidal silicon dioxide, starch or mannitol. In this second instance kneads are obtained which are granulated and distributed in sachets or used for preparing tablets.

The oral absorption of HCA suspended in different lipophilic carriers was compared with that of an aqueous solution thereof. For this purpose, groups of male rats (Sprague-Dawley, 180–220 g) fasting from the evening before the test, were treated by gastric tube with a single dose of 4% HCA suspension or solution (400 mg/kg; 10 ml/kg) in the following preparations:

A—Suspension in peanut oil
B—Suspension in a 85:15 peanut oil: GPGI* mixture
C—Suspension in soybean oil
D—Suspension in liquid paraffin
E—Suspension in fractionated coconut oil
F—Suspension in a 85:15 fractionated coconut oil: GPGI* mixture
G—Suspension in GPGI*
H—Aqueous suspension.

* GPGI=unsaturated polyglycolised glycerides.

At pre-established times (0, 15, 30, 60, 120, 240, 360, 480 minutes) the blood samples (300 μl) were taken from the retro-orbital venous sinus in rats under slight ether anaesthesia. The plasma obtained by centrifugation was then analyzed for its anthocyanosides content by spectrophotometric method (P. Morazzoni et al., Arzneim. Forsch./Drug Res., 41, 128–131, 1991) using as reference a standard scale of anthocyanosides (HCA) in control plasma.

$C_{max}$, area under the curve (AUC) and relative bioavailability (R.B.) of the suspensions A-G versus the aqueous solution H were then calculated according to the following formula:

$$R.B. = \frac{AUC\ (0\text{--}480')\ susp.\ A\text{-}G/Dose\ HCA}{AUC\ (0\text{--}480')\ aq.\ sol.\ H/Dose\ HCA}$$

Surprisingly, anthocyanosides plasma levels remarkably higher than those found for the other preparations were obtained only with preparation E (HCA suspension in fractionated coconut oil). Particularly, the relative bioavailability value (R.B.) of suspension E in comparison to the aqueous solution H turned out to be 8.77.

The marked bioavailability increase is maintained or even improved by administering 6% (R.B.=10.8) and 8% (R.B.=7.8) HCA suspensions, always in fractionated coconut oil.

An increase in the pharmacological activity in the test of capillary fragility follows the bioavailability increase. Male guinea-pigs weighing about 250 g were fed for two weeks with a low content Vitamin C diet (10 mg/kg) so as to obtain animals with reduced capillary resistance. The measure of the capillary resistance was carried out by means of the Charlier vacuometer and it is defined as the depression (in cmHg) which, applied on the animal cutis, causes the appearance of at least 3–4 petechias (R. Charlier et al., Arch. Int. Physiol. Biochim. 71, 1, 1963). The animals were orally treated once a day for three consecutive days with HCA dissolved in water or suspended in fractionated coconut oil.

The results reported in Table 2 show that the suspension in fractionated coconut oil is more active than the aqueous solution. The potency ratio calculated 4 hours after the last administration was about 3.5.

From the obtained pharmacokinetic and pharmacological data, the HCA suspension in fractionated coconut oil proves to be remarkably and surprisingly more bioavailable than the aqueous solutions or suspensions in other vegetable or mineral oils.

It is known that the bioavailability of water-insoluble, but lipophilic drugs, can be enhanced by formulating them in suitable oily carriers (H. de Nijs, Acta Pharm. Technol., 33(4), 163-168, 1987).

According to the present formulations the HCA, water-soluble and poorly lipophilic, are better absorbed when formulated in an oily suspension in fractionated coconut oil.

The following examples further illustrate the invention.

EXAMPLE 1

Gelatine capsules containing 25 mg of *V. myrtillus* anthocyanosides.

| One capsule contains: | |
|---|---|
| 90% HCA | 27.8 mg |
| Fractionated coconut oil | 472 mg |

27 8 g of HCA are dispersed in 472 g of fractionated coconut oil by means of turbine stirrer, at room temperature, until an homogeneous suspension is obtained, which is deaerated under vacuum and distributed in capsules, dosing at 500 mg/capsule.

EXAMPLE 2

Sachets of granulate containing 30 mg of *V. myrtillus* anthocyanosides.

| One sachet contains: | |
|---|---|
| 95% HCA | 31.6 mg |
| Fractionated coconut oil | 500 mg |
| Mannitol | 468.4 mg |
| Colloidal silicon dioxide | 420 mg |
| Pregelatinized starch | 210 mg |
| Polyvinylpyrrolidone | 200 mg |
| Talc | 59.7 mg |
| Methacrylic acid copolymer (type C) | 47 mg |
| Triethyl citrate | 9.4 mg |
| Polyethylene glycol 6000 | 3.5 mg |
| Simethicone emulsion | 0.4 mg |
| Flavour | 45 mg |
| Saccharin sodium | 5 mg |

31.6 g of HCA are dispersed in 500 g of fractionated coconut oil with a turbine stirrer at room temperature. 468.4 g of mannitol, 420 g of colloidal silicon dioxide and 210 g of pregelatinized starch are mixed and the HCA suspension in fractionated coconut oil is slowly added kneading in high speed mixer. A 200 g polyvinylpyrrolidone solution in 600 g of alcohol is slowly added to the mixture, which is then granulated through a 30 mesh sieve and dried under vacuum. The granulate is coated in fluid bed with an aqueous suspension containing polyethylene glycol 6000, triethyl citrate, simethicone emulsion, talc and methacrylic acid copolymer. The coated granulate is added with flavour, saccharin sodium and distributed in sachets, dosing at 2 g/sachet.

EXAMPLE 3

Tablets containing 15 mg of *R. nigrum* anthocyanosides.

| One tablet contains: | |
|---|---|
| 80% HCA | 18.8 mg |
| Fractionated coconut oil | 250 mg |
| Mannitol | 231.1 mg |
| Colloidal silicon dioxide | 220 mg |
| Pregelatinized starch | 105 mg |
| Polyvinylpyrrolidone | 100 mg |
| Talc | 29.9 mg |
| Methacrylic acid copolymer (type C) | 23.5 mg |
| Triethyl citrate | 4.7 mg |
| Polyethylene glycol 6000 | 1.8 mg |
| Simethicone emulsion | 0.2 mg |
| Sorbitol | 90 mg |
| Cross-linked sodium carboxymethylcellulose | 20 mg |
| Magnesium stearate | 5 mg |

18.8 g of HCA are dispersed in 250 of fractionated coconut oil by means of turbine stirrer at room temperature. 231.1 g of mannitol, 210 g of colloidal silicon dioxide and 105 g of pregelatinized starch are mixed and the HCA suspension in fractionated coconut oil is slowly added kneading in high speed mixer. A 100 g polyvinylpyrrolidone solution in 300 g of alcohol is slowly added to the mixture which is granulated through a 30 mesh sieve and dried under vacuum. The granulate is coated in fluid bed with an aqueous suspension of polyethylene glycol 6000, triethyl citrate, simethicone emulsion, talc and methacrylic acid copolymer. The coated granulate is added with sorbitol, cross-linked sodium carboxymethylcellulose, colloidal silicon dioxide and magnesium stearate and mixed in a cube mixer. The mixture is tabletted dosing at 1.1 g/tablet

TABLE 1

| Relative bioavailability of HCA (400 mg/kg, 10 mL/kg) in the rat. | | | | |
|---|---|---|---|---|
| Treatment | n° animals | $C_{max}$ µg/mL | AUC (0–480 min) µg min/mL | Relative bioavailability |
| Suspension in: | | | | |
| A  peanut oil | 10 | 1.31 ± 0.08 | 222.7 ± 38.8 | 0.90 |
| B  peanut oil: GPGI (85:15) | 10 | 1.89 ± 0.20 | 349.0 ± 61.8 | 1.41 |
| C  soybean oil | 10 | 1.80 ± 0.17 | 334.1 ± 24.3 | 1.35 |
| D  liquid paraffin | 10 | 1.70 ± 0.20 | 222.7 ± 30.9 | 0.90 |
| E  fractionated coconut oil | 10 | 10.73 ± 3.33 | 2170.2 ± 567.2 | 8.77 |
| F  fractionated coconut oil: GPGI (85:15) | 10 | 6.40 ± 1.28 | 735.1 ± 139.2 | 2.47 |
| G  GPGI | 10 | 3.98 ± 0.77 | 594.0 ± 173.3 | 2.15 |
| Solution in: | | | | |
| H  water | 10 | 1.06 ± 0.14 | 247.5 ± 38.2 | 1.00 |

TABLE 2

| Treatment | Dose mg/kg/die os | n. animals | Capillary resistance in cm Hg (m ± e.s.) Day 1-hours after treatment | | | |
|---|---|---|---|---|---|---|
| | | | 0 | 2 | 4 | 6 |
| Controls (coconut oil) | 10 mL/kg | 6 | 15.8 ± 0.4 | 16.2 ± 0.4 10% | 15.8 ± 0.4 0% | 15.8 ± 0.4 0% |
| HCA susp. in fractionated coconut oil | 100 | 6 | 15.8 ± 0.4 | 17.0 ± 0.7 31% | 17.2 ± 1.0 36% * | 16.7 ± 0.8 23% * |
| | 200 | 6 | 16.0 ± 0.6 | 17.8 ± 0.5 49% | 18.8 ± 0.5 76% | 18.3 ± 0.6 62% |
| Controls (water) | 10 mL/kg | 6 | 16.2 ± 0.4 | 15.8 ± 0.5 −11% | 16.0 ± 0.5 −6% | 15.8 ± 0.5 −11% |
| HCA water solution | 200 | 6 | 15.8 ± 0.4 | 16.8 ± 0.7 26% | 17.0 ± 0.4 31% * | 16.8 ± 0.4 26% |
| | 400 | 6 | 16.0 ± 0.4 | 17.0 ± 0.4 27% | 18.7 ± 0.5 73% | 17.0 ± 0.6 27% |

| Treatment | Dose mg/kg/die os | n. animals | Capillary resistance in cm Hg (m ± e.s.) Day 3-hours after treatment | | | |
|---|---|---|---|---|---|---|
| | | | 0 | 2 | 4 | 6 |
| Controls (coconut oil) | 10 mL/kg | 6 | 15.8 ± 0.4 0% | 15.8 ± 0.4 0% | 16.0 ± 0.4 5% | 16.0 ± 0.4 5% |
| HCA susp. in fractionated coconut oil | 100 | 6 | 16.8 ± 0.5 26% | 17.2 ± 0.5 36% | 16.3 ± 0.4 13% | 15.8 ± 0.4 0% |
| | 200 | 6 | 17.3 ± 1.0 35% | 17.3 ± 1.0 35% | 18.5 ± 0.9 68% | 17.3 ± 0.6 35% |
| Controls (water) | 10 mL/kg | 6 | 16.2 ± 0.4 0% | 16.1 ± 0.4 −3% | 16.3 ± 0.4 3% | 16.1 ± 0.4 −3% |
| HCA water solution | 200 | 6 | 17.0 ± 0.7 31% | 17.6 ± 0.9 46% | 15.8 ± 0.4 0% | 15.8 ± 0.4 0% |
| | 400 | 6 | 17.2 ± 0.5 32% | 17.3 ± 0.8 35% | 16.8 ± 0.5 22% | 16.3 ± 0.5 8% |

*$p < 0.05$ Dunnett's t test versus controls
Percent variation = $C.R._T - C.R._B)/(C.R._N - C.R._B) \cdot 100$ where:
$C.R._T$ = mean capillary resistance after treatment.
$C.R._B$ = mean basal capillary resistance after low Vitamin C content diet.
$C.R._N$ = mean normal capillary resistance (=19.7 cm Hg) before the low Vitamin C content diet.

We claim:

1. A pharmaceutical composition for oral administration containing as the active principle an anthocyanoside extract (HCA) containing more than 50% w/w of anthocyanosides suspended in from 2 to 10% (w/w) of fractionated coconut oil where in said anthocyanoside extract is obtained from the fruits of vaccinum myrtillus, Ribes nigrum, Vitis Vinefera or Sambcus nigra.

2. The composition according to claim 1 which contains more than 80% of said anthocyanosides.

3. The composition according to claim 1 which includes soybean lecithin as the surfactant and at least one of colloidal silicon dioxide, starch and mannitol.

4. The composition according to claim 3 in the form of a capsule, a sachet or a tablet.

5. The composition according to claim 3 which is in the form of a gelatine capsule containing 90% by weight of said anthocyanoiside.

6. The composition according to claim 4 which is in the form of a sachet, containing 95% of an anthocyanoiside extract from *V. myrtillus*, fractionated coconut oil, colloidal silicon dioxide, mannitol, pregelatinized starch, polyvinylpyrrolidone, talc, triethyl citrate, polyethylene glycol 6000, simethicone emulsion, a flavoring agent methacrylic acid copolymer (type C) and sodium saccharin.

7. The composition according to claim 4 which is in the form of a tablet containing 80% of the anthocyanoside extract from *R. nigrum*, fractionated coconut oil, mannitol, colloidal silicon dioxide, pregelatinized starch, polyvinylpyrrolidone, talc, methacrylic acid copolymer (type C), triethyl citrate, polyethylene glycol, simethicone emulsion, sorbitol, cross-linked sodium carboxymethylcellulose and magnesium stearate.

* * * * *